United States Patent [19]

Takematsu et al.

[11] Patent Number: 4,685,962
[45] Date of Patent: Aug. 11, 1987

[54] PHENYLACETANILIDE DERIVATIVES

[75] Inventors: Tetsuo Takematsu, Utsunomiya; Akinori Suzuki, Chiba; Kazuya Toda; Masuo Goto, both of Nagano, all of Japan

[73] Assignee: Yashima Chemical Industrial Co., Ltd., Tokyo, Japan

[21] Appl. No.: 682,762

[22] Filed: Dec. 17, 1984

[30] Foreign Application Priority Data

Dec. 26, 1983 [JP] Japan .................. 58-244071

[51] Int. Cl.⁴ .................. A01N 37/22; C07C 103/85; C07C 103/78; C07C 103/76
[52] U.S. Cl. .................. 71/118; 564/170; 564/182
[58] Field of Search .................. 564/182, 170; 71/118

[56] References Cited

U.S. PATENT DOCUMENTS

| | | | |
|---|---|---|---|
| 3,366,674 | 1/1968 | Geiger | 564/182 X |
| 4,386,080 | 5/1983 | Crossley et al. | 564/170 X |
| 4,453,975 | 6/1984 | Takematsu et al. | 564/182 X |
| 4,455,164 | 6/1984 | Takematsu et al. | 564/182 X |
| 4,484,942 | 11/1984 | Kirino et al. | 564/182 X |
| 4,536,346 | 8/1985 | Shepherd et al. | 564/182 X |

FOREIGN PATENT DOCUMENTS

| | | | |
|---|---|---|---|
| 61583 | 10/1982 | European Pat. Off. | |
| 58-43943 | 3/1983 | Japan | 564/182 |
| 59-79045 | 4/1984 | Japan | 564/182 |

*Primary Examiner*—Charles F. Warren
*Assistant Examiner*—Carolyn S. Greason
*Attorney, Agent, or Firm*—Wenderoth, Lind & Ponack

[57] ABSTRACT

A compound of the formula

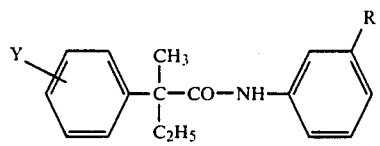

wherein Y represents a halogen atom, a lower alkyl group, a lower alkoxy group or a trifluoromethyl group and R represents a lower alkyl group. This compound can be produced by reacting a compound of the formula

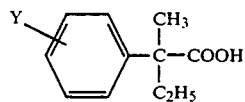

or a reactive derivative thereof with an aniline derivative of the formula

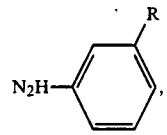

and is useful as a herbicide.

8 Claims, No Drawings

PHENYLACETANILIDE DERIVATIVES

This invention relates to a novel phenylacetanilide derivative, more specifically an alpha-methyl-alpha-ethyl phenylacetanilide derivative represented by the following formula

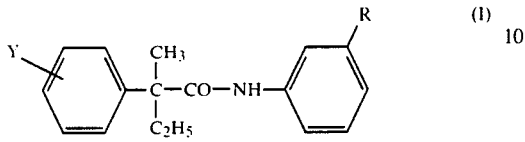

wherein Y represents a halogen atom, a lower alkyl group, a lower alkoxy group or a trifluoromethyl group and R represents a lower alkyl group,
a process for production thereof, and the use thereof as a herbicide.

We previously disclosed that certain alpha,alpha-dimethylphenylacetanilide derivatives are useful as herbicides (see U.S. Pat. No. 4,453,975).

We have now found that the compounds of the above formula (I) are novel compounds not described in the prior literature, and that these compounds exhibit excellent selective biological activities on plants, and particularly when used as herbicides for rice paddies, do not cause any substantial phytotoxicity to useful crops but show strong herbicidal activity and growth inhibiting activity against competing weeds such as barnyard grass (*Echinochloa crus-galli* Beauv.), umbrella plant (*Cyperus difformis* L.) and water nutgrass (*Cyperus serotinus* Rottb.).

The term "lower", as used in the present specification and the appended claims, means that a group of compound qualified by this term has not more than 4, preferably not more than 3, carbon atoms.

The lower alkyl group in formula (I) may be linear or branched, and includes, for example, methyl, ethyl, propyl, isopropyl, butyl, isobutyl, sec-butyl and tert-butyl. The lower alkoxy group is a lower alkyloxy group in which the lower alkyl moiety is as defined above, and includes, for example, methoxy, ethoxy, propoxy, isopropoxy and butoxy.

The halogen atom includes fluorine and chlorine.

In the compounds of formula (I), Y is preferably a fluorine atom, an alkyl group having 1 to 3 carbon atoms, an alkoxy group having 1 to 3 carbon atoms or a trifluoromethyl group, and more preferably a methyl or methoxy group. The substituent Y can be present at any desired site on the benzene ring, preferably at the 2-position of the benzene ring.

Preferred substituents R are ethyl and n-propyl groups, especially an n-propyl group.

The compounds of formula (I) provided by this invention can be prepared, for example, by reacting an alpha-methyl-alpha-ethyl substituted phenylacetic acid or its reactive derivative, typically a compound of the following formula

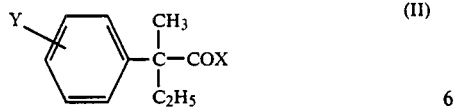

wherein X represents a halogen atom, especially chlorine or bromine, a lower alkoxy group (e.g., methoxy or ethoxy) or a hydroxyl group, and Y is as defined above,
with an aniline derivative of the following formula

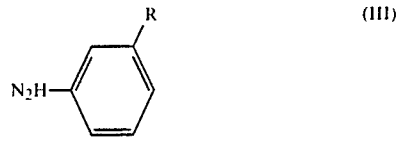

wherein R is as defined above.

The reaction of the compound of formula (II) with the aniline derivative of formula (III) can be carried out in the absence of solvent. Generally, however, it is carried out in an inert medium. Examples of the inert medium include aromatic hydrocarbons such as benzene, toluene and xylene, ethers such as diethyl ether, tetrahydrofuran and dioxane, alcohols such as diethylene glycol and ethylene glycol, ketones such as acetone and methyl ethyl ketone, halogenated hydrocarbons such as methylene chloride, chloroform and carbon tetrachloride, and esters such as ethyl acetate and ethyl propionate. Benzene, toluene and ethyl acetate are especially suitable.

The reaction temperature is not critical and can be varied widely depending upon the type of the starting materials and/or the solvent. Generally, temperatures ranging from about 0° C. to the refluxing temperature of the reactant mixture are advantageously used.

The reaction pressure is usually atmospheric pressure, but as required, the reaction can be performed under reduced or elevated pressures.

The reaction can be carried out in the presence of general reaction aids depending upon the type of the compound of formula (II). For example, when X represents a halogen atom in formula (II), we use some reaction aids. Examples of the reaction aids include alkali metal hydroxides such as sodium hydroxide and potassium hydroxide, organic bases such as pyridine, N,N-dimethylaniline, triethylamine and tripropylamine, and alkali metal carbonates such as sodium hydrogen carbonate. We also use some reaction aids when X represents a hydroxyl group in formula (II). Examples of the reaction aids in this case include dehydrating agents such as dicyclohexylcarbodiimide, sulfuric acid and p-toluenesulfonic acid. When X represents an alkoxy group, we use such a reaction aid as sodium methoxide.

The amount of the reaction aids is desirably about 0.05 to 1.2 equivalents per mole of the compound of formula (II).

Advantageously, the aniline derivative of formula (III) is used in an amount of about 1.0 to 1.2 moles for each 1.0 mole of the compound of formula (II).

Under the conditions described above, the reaction ends in about 0.5 to 10 hours. The desired compound of formula (I) may be recovered from the reaction mixture and purified by methods known per se, for example by recrystallization (benzene, toluene, methanol, ethanol, chloroform, hexane, ethyl acetate, etc. are advantageously used as recrystallization solvents), distillation, chromatography, etc.

The compound of formula (II) used as a starting material in the above reaction, i.e. an alpha-methyl-alpha-ethyl substituted phenylacetic acid, an alpha-methyl-alpha-ethyl substituted phenylacetic acid halide or an alpha-methyl-alpha-ethyl substituted phenylacetic acid ester, is known per se, or can be produced by methods known per se. For example, the alpha-methyl-alpha-ethyl substituted phenylacetic acid halide can be produced in a customary manner by reacting the alpha-methyl-alpha-ethyl substituted phenylacetic acid with a halogenating agent such as thionyl chloride, phosphorus trichloride, phosphorus tribromide or phosphorus pentachloride. The alpha-methyl-alpha-ethyl substituted phenylacetic acid ester can be produced generally by dehydrocondensing the alpha-methyl-alpha-ethyl substituted phenylacetic acid with an alcohol such as methanol or ethanol.

The production of the compound of formula (I) is illustrated below specifically by examples.

PREPARATION EXAMPLE 1

Preparation of compound No. 4

A 100 ml four-necked flask was charged with 50 ml of benzene, 2.20 g (0.01 mole) of alpha-methyl-alpha-ethyl-p-isopropylphenylacetic acid and 1.21 g (0.01 mole) of m-ethylaniline, and with cooling and stirring, 2,06 g (0.01 mole) of dicyclohexylcarbodiimide was added dropwise. After the addition, the mixture was stirred at room temperature for 10 hours. After the reaction, the reaction mixture was filtered through a glass filter, and the filtrate was concentrated under reduced pressure. Recrystallization of the residual crystals from a mixture of n-hexane and ethyl acetate (1:49) gave 2.76 g (yield 85.4%) of alpha-methyl-alpha-ethyl-p-isopropylphenylaceto-m-ethylanilide.

Melting point: 124°–126° C.

IR $\nu_{max}^{nujol}$ cm$^{-1}$: 1660 (C=O), 3330 (N—H).

| Elemental analysis for $C_{22}H_{29}ON$: | | | |
|---|---|---|---|
| | C | H | N |
| Calculated (%): | 81.69 | 9.04 | 4.33 |
| Found (%): | 81.57 | 8.96 | 4.35 |

PREPARATION EXAMPLE 2

Preparation of compound No. 8

A 100 ml four-necked flask was charged with 50 ml of benzene, 1.01 g (0.01 mole) of triethylamine and 1.35 g (0.01 mole) of m-(n-propyl)aniline, and with cooling and stirring in water, 2.26 g (0.01 mole) of alpha-methyl-alpha-ethyl-o-methoxyphenylacetyl chloride was slowly added dropwise. After the addition, a dehydrating tube was attached to the flask, and the mixture was stirred at room temperature for 7 hours. After the reaction, the reaction mixture was washed with water to remove triethylamine hydrochloride. The benzene layer was dried over anhydrous sodium sulfate, and the solvent was evaporated under reduced pressure. The residue was purified by silica gel column chromatography (developing solvent: n-hexane/ethyl acetate=4/1) to give 2.93 g (yield 90.19%) of alpha-methyl-alpha-ethyl-o-methoxyphenylaceto-m-(n-propyl)anilide as a white solid.

Melting point: 47°–49° C.

IR $\nu_{max}^{nujol}$ cm$^{-1}$: 1660 (C=O), 3280 (N—H).

| Elemental analysis for $C_{21}H_{27}O_2N$: | | | |
|---|---|---|---|
| | C | H | N |
| Calculated (%): | 77.50 | 8.36 | 4.30 |
| Found (%): | 77.47 | 8.38 | 4.28 |

In the same way as in Preparation Example 1 or 2, the compounds shown in Table 1 below can be produced. Table 1 also shows compounds Nos. 4 and 8.

TABLE 1

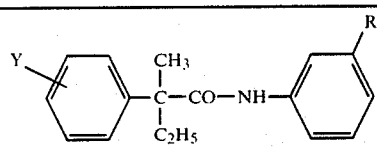

| Compound No. | Y | R | Melting point (°C.) or refractive index ($n_D^{25}$) |
|---|---|---|---|
| 1 | 2-CH$_3$ | n-C$_3$H$_7$ | $n_D^{25}$ = 1.5609 |
| 2 | 4-CH$_3$ | " | $n_D^{25}$ = 1.5616 |
| 3 | 4-iso-C$_3$H$_7$ | CH$_3$ | m.p. 131–133 |
| 4 | " | C$_2$H$_5$ | m.p. 124–126 |
| 5 | " | n-C$_3$H$_7$ | m.p. 100–101 |
| 6 | 2-OCH$_3$ | CH$_3$ | $n_D^{25}$ = 1.5676 |
| 7 | " | C$_2$H$_5$ | $n_D^{25}$ = 1.5674 |
| 8 | " | n-C$_3$H$_7$ | m.p. 47–49 |
| 9 | " | iso-C$_3$H$_7$ | $n_D^{25}$ = 1.5554 |
| 10 | 4-OCH$_3$ | n-C$_3$H$_7$ | $n_D^{25}$ = 1.5508 |
| 11 | 4-OC$_2$H$_5$ | " | $n_D^{25}$ = 1.5574 |
| 12 | 2-O—n-C$_3$H$_7$ | " | $n_D^{25}$ = 1.5484 |
| 13 | 4-Cl | C$_2$H$_5$ | $n_D^{25}$ = 1.5691 |
| 14 | " | n-C$_3$H$_7$ | $n_D^{25}$ = 1.5704 |
| 15 | 2-F | C$_2$H$_5$ | m.p. 57–58 |
| 16 | " | n-C$_3$H$_7$ | m.p. 72.5–73.5 |
| 17 | 3-CF$_3$ | " | $n_D^{25}$ = 1.5154 |

The compounds of formula (I) provided by this invention have superior herbicidal activities, and are useful as active ingredients of herbicides for controlling various weeds in agricultural crops. Examples of weeds which can be controlled by the compounds of formula (I) are various species of barnyard grass (such as *Echinochloa crus-galli* Beauv., *Echinochloa crus-galli* var. oryzicola Ohwi, and *Echinochloa crus-galli* Subsp. genuina var. echinata Honda), spikerush (*Eleocharis pellucida* Presl), sedge sp. (*Cyperus hakonensis* Saiat), umbrella plant (*Cyperus difformis* L.), pipewort (*Eriocaulon sieboldtianum* Sieb), waterwort (*Elatine triandra*), redstem sp. (*Rotala indica* Koehne), bulrush (*Scirpus juncoides* Roxb), redstem sp. (*Ammannia multiform* Roxb.), false pimpernel (*Lindernia pyxidaria* L), and slender spikerush (*Eleocharis acicularis* Roem. et Schalt var. longiseta Svenson). These examples are not limitative, and it should be understood that the compounds of formula (I) exhibit herbicidal effects also against other kinds of weeds.

It has been found that the compounds of formula (I) exhibit marked effects in controlling weeds which occur in fields containing much water, such as a paddy field, rather than those which occur in dry upland fields.

Thus, the compounds of formula (I) exhibit excellent control effects against various species of barnyard grass, especially *Echinochloa crus-galli* Beauv. which is a very hazardous weed in an aquatic paddy and is considered as one of the five greatest weeds in the world. This weed grows in paddy fields, especially submerged paddy fields, throughout the world. The compounds of formula (I) have the ability to inhibit the germination of the barnyard grass strongly and to prevent its growth in paddy fields.

Moreover, the compounds of formula (I) are very characteristic in that they have excellent selective herbicidal activity which ensures substantial freedom from phytotoxicity to useful agricultural crops such as rice.

Many herbicides have heretofore been suggested for application to paddy fields, and some have come into actual use. Almost none of them, however, have selectivity in physiological herbicidal action between barnyard grass and rice plant. The conventional methods for weed killing in paddy fields are directed to the treatment of paddy fields in the rice growing stage (including the transplanting stage) to control the sprouting of barnyard grass. They are based either on the utilization of the differences in resistance to herbicides between barnyard grass and rice plant according to the differences in their growing stages, or on the principle of chemical adsorption in the upper layer of soil ("artificial selectivity") whereby rice plants are transplanted in such a manner that their roots are located below the herbicide-treated layer, and barnyard grass in the upper layer is controlled while protecting the rice plants from the herbicide.

Barnyard grass is a gramineous weed, as is rice, and they physiologically resemble each other. Hence, controlling of barnyard grass with herbicidal chemicals often causes phytotoxicity to rice plant, and it is extremely difficult to control this weed selectively in paddy fields. Barnyard grass has therefore been considered to be difficult to eradicate in paddy fields, and there has been a strong demand for the advent of herbicides which can selectively control barnyard grass.

The compounds of formula (I) meet this demand of agriculture. They have excellent intergenus selective activity on gramineous plants, and while they cause substantially no phytotoxicity to rice, they have strong inhibiting activity against barnyard grass which is a plant of the family Gramineae but belongs to a different genus from rice. In addition, they exhibit excellent herbicidal activity and growth-inhibiting activity against weeds of the family Cyperaceae such as water nutgrass and umbrella plant. Further, they have the excellent property of acting selectively on the seeds and seedlings of barnyard grass to strongly inhibit their germination, but causing no substantial phytotoxicity to rice plant. This property makes the compounds of formula (I) very suitable as active ingredients of herbicides for application to paddy fields.

The superior herbicidal activity of the compounds (I) can be demonstrated by the experimental fact that when alpha-methyl-alpha-ethyl-o-methoxyphenyl-aceto-m-(n-propyl)anilide was applied at a rate of 31.25 g per 10 acres to a paddy field where rice plant and barnyard grass were simultaneously sown, the germination of the barnyard grass was completely inhibited, whereas the rice plant showed normal emergence and growth without any phytotoxicity, and that even when the rate of the compound applied was increased to 300 g per 10 ares, the rice plant showed normal germination and growth without any phytotoxicity. Thus, the compound of formula (I), when applied in an amount about 20 times as large as the amount required for completely controlling barnyard grass, does not exert any substantial effect on the germination and growth of rice plant.

Such a high selectivity of the compounds in accordance with this invention between barnyard grass and rice plant is ascribable presumably to the specific physiological activities of the compounds against barnyard grass and rice plant. This superior selectivity cannot be expected from the conventional herbicides available for application to paddy fields.

The compound of formula (I) may be applied directly as a herbicide. Generally, however, it is formulated into a herbicidal composition by mixing it with inert liquid or solid carriers or diluents which are commonly employed in herbicide formulations.

In the present invention, any inert liquid or solid agriculturally acceptable carriers or diluents known in the art can be used. Examples of the inert solid carrier or diluent are kaolin, diatomaceous earth, talc bentonite, silica, calcium carbonate and clay materials. Examples of the inert liquid carrier or diluent are water, xylene, toluene, benzene, kerosene, ethyl acetate, methanol, ethanol, N,N-dimethyl formamide, dimethyl sulfoxide, and liquefied gases such as tetrafluoroethane.

In addition to the inert liquid or solid carrier or diluent, the herbicidal composition may, as needed, contain nonionic, anionic, cationic or amphoteric surface-active agents such as polyoxyethylene alkyl ethers, polyoxyethylene alkyl aryl ethers, polyoxyethylene fatty acid esters, alkylsulfonate salts, alkyldimethyl benzyl ammonium chlorides, alkyl dimethylbetaines and polyoxyethylene alkylsulfate esters, and/or polymeric compounds such as carboxy methyl cellulose, polyvinyl alcohol and sodium alginate, in usual amounts chosen according to the form of the herbicidal composition.

The herbicidal composition may contain the active compound of formula (I) in an amount of at least 0.3% by weight, preferably 0.5 to 99% by weight, more preferably 1 to 90% by weight, based on the weight of the composition itself.

The herbicidal composition can be in any conventional forms as a dust, granule, wettable powder, solution, emulsifiable concentrate, or spray according to the method of application. Any methods of formulation known in that art can be used for this purpose. For example, when making a dust, granule or wettable powder, at least one active compound of formula (I) is mixed with at least one inert solid carrier or diluent. The mixture is pulverized and mixed uniformly with a suitable amount of a surface active agent. The solution or emulsifiable concentrate can be prepared by dissolving or dispersing at least one active compound of formula (I) in at least one inert liquid carrier or diluent, followed, if desired, by adding a surface active agent.

Conveniently, the amount of the active compound of formula (I) is 0.5 to 20% by weight for the dust and granule,, 10 to 80% by weight for the wettable powder, and 1 to 50% by weight for the solution and emulsifiable concentrate, all based on the weight of the resulting composition.

The herbicidal composition may further contain agricultural chemicals commonly used in cultivating agricultural crops, such as fungicides, insecticides, nematocides, plant growth controlling agents and fertilizers. Typical examples of the fungicides are Benomyl [methyl 1-(N-butylaminocarbonyl)-1H-benzimidazol-2-yl-carbamate], Hymexazol (5-methyl-3-isoxazolol), Captan [3a,4,7,7a-tetrahydro-N-(trichloromethanesulphenyl)phthalimide], and Zineb [zinc ethylenebis(dithiocarbamate)]. Examples of the insecticides are Disulfoton (O,O-diethyl S-2-ethylthioethyl phosphorodithioate) and Propoxur (2-isopropoxyphenyl methylcarbamate). Examples of the nematocides are Methomyl [S-methyl N-(methylcarbamoyloxy)thioacetamidate] and Alidicarb [2-methyl-2-(methylthio)propionaldehyde O-methylcarbamoyloxime].

It is also possible to incorporate at least one other herbicidally active compound used heretofore in the art into the herbicidal composition of this invention. This frequently brings about a high herbicidal effect against a broad spectrum of weeds. Examples of the other herbicidally active compounds are given below. It should be understood that these examples are not limitative, and other active compounds can be equally incorporated in the herbicidal composition of this invention as required.

Phenoxycarboxylic acid-type herbicides such as 2,4-dichlorophenoxyacetic acid, allyl 2-methyl-4-chlorophenoxyacetate, S-ethyl 2-methyl-4-chlorophenoxyacetate, 2-methyl-4-chlorophenoxyacetic acid (including its esters and salts) and 2-methyl-4-chlorophenoxybutyric acid (including its esters and salts); diphenyl ester-type herbicides such as 3-methyl-4'-nitrodiphenyl ether, 2,4-dichlorophenyl-4'-nitrophenyl ether, 2,4,6-trichlorophenyl-4'-nitrophenyl ether, 2-chloro-4-trifluoromethylphenyl-3'-ethoxy-4'-nitrophenylether, 2,4-dichlorophenyl-4'-nitro-3'-methoxyphenyl ether and 2,4-dichlorophenyl-3'-methoxycarbonyl-4'-nitrophenyl ether; organophosphorus-type herbicides such as O-ethyl-O-(2-nitro-5-methylphenyl)N-secondary butyl phosphoroamidothioate, S-(2-methyl-1-piperidylcarbonylmethyl) O,O-di-n-propyldithiophosphate, and O,O-diisopropyl-2-(benzenesulfonamido)ethyldithiophosphate; thiolcarbamate-type herbicides such as S-(4-chlorobenzyl)-N,N-diethylthiolcarbamate, S-benzyl-N-ethyl-N-isobutylthiolcarbamate, S-ethyl-N,N-hexamethylenethiolcarbamate and S-isopropyl-N,N-hexamethylenethiolcarbamate; urea-type herbicides such as 1-(2,2-dimethylbenzly)-3(p-tolyl)urea and N-$\alpha,\alpha$-dimethylbenzyl-$\alpha$-bromo-t-butylacetamide; triazine-type herbicides such as 2-methylthio-4,6-bis-ethylamino-1,3,5-triazine, 2-methyl-thio-4,6-bis-isopropylamino-1,3,5-triazine, 2-methylthio-4-ethylamino-6-(1,2-dimethylpropylamino)-1,3,5-triazine and 2-methylthio-4-ethylamino-6-isopropylamino-1,3,5-triazine; amide-type herbicides such as 3,4-dichloropropionanilide, $\alpha$-($\beta$-naphthoxy)propionanilide, 2-chloro-2',6'-diethyl-N-(butoxymethyl)acetanilide, 2-chloro-2',6'-diethyl-N-(propoxyethyl)acetanilide and 2-($\alpha$-naphthoxy)-N,N-diethylpropionamide; pyrazol-type herbicides such as 4-(2,4-dichlorobenzoyl)-1,3-dimethyl-5-pyrazolyl-4-toluenesulfonate and 1,3-dimethyl-4-(2,4-dichlorobenzoyl)-5-benzoyl-methoxypyrazole; and other herbicides such as 5-t-butyl-3 -(2,4-dichloro-5-isopropoxyphenyl)-1,3,4-oxadiazolin-2-one, 3-isopropyl-1H-2,1,3-benzothiaziadin(4)-3H-one-2,2-dioxide, and 2-amino-1,3-chloro-1,4-naphthoquinone.

The herbicidal compositions of this invention containing these other herbicidally active compounds are especially useful for application to paddy fields in the rice growing stage, for example to a paddy field in which transplantation has ended.

The herbicide containing the compound of formula (I) as an active ingredient can be used to control various weeds in areas where agricultural crops are cultivated. In particular, the herbicide of this invention is effective against weeds in wet paddies rather than dry fields, and exhibits a very strong selective herbicidal effect against barnyard grass which accompanies rice plant in paddy fields, such as *Echinochloa crus-galli Beauv.*

Herbicides containing as active ingredients 2,4,6-trichlorophenyl-4'-nitrophenyl ether (MO or CNP), S-(4-chlorobenzyl)-N,N-diethylthiocarbamate (Benthiocarb), 2-chloro-2',6'-diethyl-N-(butoxymethyl)acetanilide (Butachlor), and S-ethyl-N,N-hexamethylenethiocarbamate (Molinate), which now gain widespread acceptance for application to paddy fields, do not show selectivity between barnyard grass and rice plant in the germinating stage, nor are they absolutely safe to transplanted rice plants in the early stage of growth. With these conventional herbicides, the risk of phytotoxicity cannot be avoided in the event of changes in the environmental condition of paddy fields, for example when rice plants are transplanted shallow at the soil surface, the soil is sandy, the water leaks, root growth is absormal, or the temperature becomes unusually high.

Since the herbicide provided by this invention is based on physiological selectivity, it has the advantage of being applicable to all growing stages of rice plants ranging from the germination to the growing stage, and being substantially free from phytotoxicity to rice plants by changes in environmental conditions. Thus, it contributes greatly to the cultivation of agricultural crops.

Heretofore, 3',4'-dichloropropionanilide (Propanil) has been used worldwide as an agent having selective activity against barnyard grass in a paddy field. Propanil, however, is an agent suited for foliar application and has no effect of inhibiting germination. In contrast, the herbicide of this invention exhibits far higher selective activity during the emergence of barnyard grass and rice plant than propanil, and it is no exaggeration to say that the herbicide of this invention is an epoch-making weed killer having no equal among known herbicides of this kind.

In use, the herbicide of this invention containing the active ingredient of formula (I) is applied to the locus to be protected from weeds.

The time of application of the compound of formula (I) is not strictly limited, and differs according to the agricultural crops and/or the weeds to be controlled. Generally, in order for the active compound of formula I to exhibit the best herbicidal effect, it is most convenient to apply it just before the weeds to be controlled sprout, or during their germinating stage. It is of course possible to apply it to weeds after emergence, and this brings about some extent of control effect.

There is no particular restriction on the locus to which the active compound of this invention can be applied. It can be applied to various types of agricultural land as is the case with conventional herbicides. It can be best applied however to wet paddies, especially aquatic paddies in the submerged state, and when applied to upland fields of low water content, the active compound of this invention tends to have a somewhat decreased herbicidal effect.

For the greatest herbicidal effect, the herbicide of this invention is applied to a field in a submerged condition before or during the germination of weeds.

The active compounds of formula (I) of this invention exhibit herbicidal effects against the various weeds described hereinabove, but have excellent effects of inhibiting germination of various kinds of barnyard grass, especially *Echinochloa crus-galli Beauv*, which accompany rice plants, without any substantial toxicity to rice plant. Thus, the active compounds formula (I) can be effectively applied to control barnyard grass selectively and protect rice plants therefrom.

The rate of application of the active compound of formula (I) is not critical, and can be varied widely according to the type of the active compound, the time of application, the procedure of application, etc. Advantageously, it is generally at least 10 g, preferably 20 g to 500 g, more preferably 20 g to 300 g, per 10 ares.

The method of application may be any conventional method. For example, the herbicidal composition of this invention may be sprayed onto the locus to be protected from weeds from above the ground or from the air. Or it may be sprayed together with the seeds of an agricultural crop at the time of seeding the crop.

Furthermore, according to the present invention, seeds of a crop may be dipped prior to sowing in an aqueous liquid containing the active compound of formula (I) to control the germination of weed seeds that may be present in admixture with the crop seeds.

The active compounds of formula (I) have little toxicity to useful agricultural crops and low mammalian toxicity, and therefore are very suitable as herbicides.

The following Examples further illustrate the formulation of the herbicides provided by the present invention, and their selective herbicidal activities.

In these Examples, all parts are by weight. The numbers of the compounds refer to those given in Table 1.

FORMULATION EXAMPLE 1

| Granules: | |
|---|---|
| | Parts |
| Compound No. 1 | 5 |
| Sodium dodecylbenzenesulfonate | 2 |
| Sodium laurylsulfate | 1 |
| Talc | 20 |
| Bentonite | 72 |

The above ingredients were mixed and kneaded with a suitable amount of water. The mixture was granulated by a granulator, dried and classified to obtain granules.

FORMULATION EXAMPLE 2

| Emulsifiable concentrate: | |
|---|---|
| | Parts |
| Compound No. 11 | 30 |
| Polyoxyethylene alkylaryl ether | 10 |
| Xylene | 60 |

The above ingredients were mixed to obtain an emulsifiable concentrate.

FORMULATION EXAMPLE 3

| Wettable powder: | |
|---|---|
| | Parts |
| Compound No. 17 | 50 |
| Polyvinyl alcohol | 2 |
| Sodium dodecylbenzenesulfonate | 3 |
| Diatomaceous earth | 45 |

The above ingredients were mixed and pulverized to obtain a wettable powder.

TEST EXAMPLE

Soil of an aquatic paddy was filled in pots (1/5,000 ares). Rice plants in the two-leaf stage were transplanted in the pots, seeds of barnyard grass, umbrella plant and bulrush were sown, and tubers of water-nut grass were planted. The pots were watered to provide a water depth of 3 cm. On the third day after the germination of the weeds, the watered soil was treated with a predetermined amount of a wettable powder of each of the compounds indicated in Table 2 formulated as shown in Formulation Example 3. In the third week after treatment with the chemical, the dergrees of phytotoxicity to rice plants and herbicidal efficacy on weeds were observed, and the results are shown in Table 2.

The herbicidal efficacy was evaluated as follows:

| Index | Herbicidal afficacy |
|---|---|
| 5 | Withered |
| 4 | 80–99% inhibition |
| 3 | 60–79% inhibition |
| 2 | 40–59% inhibition |
| 1 | 20–39% inhibition |
| 0 | No inhibition |

The degree of phytotoxicity to rice was evaluated on the following standard.
- −: No injury
- ±: Slight injury
- +: Small injury
- ++: Medium injury
- +++: Heavy injury

TABLE 2

| Compound No. | Active ingredient (g/a) | Herbicidal efficacy | | | | Phytotoxicity |
|---|---|---|---|---|---|---|
| | | Barnyard grass | Umbrella plant | Bulrush | Waternut grass | |
| 1 | 50.00 | 5 | 5 | 5 | 5 | — |
| | 25.00 | 5 | 5 | 5 | 5 | — |
| | 12.50 | 5 | 5 | 5 | 5 | — |
| | 6.25 | 5 | 5 | 5 | 5 | — |
| | 3.125 | 5 | 5 | 5 | 5 | — |
| 2 | 50.00 | 5 | 5 | 5 | 5 | — |
| | 25.00 | 5 | 5 | 5 | 5 | — |
| | 12.50 | 5 | 5 | 5 | 5 | — |
| | 6.25 | 5 | 5 | 4 | 4 | — |
| | 3.125 | 5 | 4 | 4 | 4 | — |
| 3 | 50.00 | 5 | 5 | 5 | 5 | — |
| | 25.00 | 5 | 5 | 5 | 5 | — |
| | 12.50 | 5 | 5 | 4 | 4 | — |
| | 6.25 | 4 | 5 | 4 | 4 | — |
| | 3.125 | 4 | 4 | 3 | 4 | — |
| 4 | 50.00 | 5 | 5 | 5 | 5 | — |
| | 25.00 | 5 | 5 | 5 | 5 | — |
| | 12.50 | 5 | 5 | 5 | 4 | — |
| | 6.25 | 5 | 5 | 4 | 4 | — |
| | 3.125 | 4 | 5 | 4 | 4 | — |
| 5 | 50.00 | 5 | 5 | 5 | 5 | — |
| | 25.00 | 5 | 5 | 5 | 5 | — |
| | 12.50 | 5 | 5 | 5 | 5 | — |
| | 6.25 | 5 | 5 | 4 | 4 | — |
| | 3.125 | 5 | 5 | 4 | 4 | — |
| 6 | 50.00 | 5 | 5 | 5 | 5 | — |
| | 25.00 | 5 | 5 | 5 | 5 | — |
| | 12.50 | 5 | 5 | 4 | 4 | — |
| | 6.25 | 4 | 5 | 4 | 4 | — |
| | 3.125 | 4 | 5 | 4 | 4 | — |
| 7 | 50.00 | 5 | 5 | 5 | 5 | — |
| | 25.00 | 5 | 5 | 5 | 5 | — |
| | 12.50 | 5 | 5 | 5 | 5 | — |
| | 6.25 | 5 | 5 | 4 | 5 | — |
| | 3.125 | 5 | 5 | 4 | 4 | — |
| 8 | 50.00 | 5 | 5 | 5 | 5 | — |
| | 25.00 | 5 | 5 | 5 | 5 | — |
| | 12.50 | 5 | 5 | 5 | 5 | — |
| | 6.25 | 5 | 5 | 5 | 5 | — |
| | 3.125 | 5 | 5 | 5 | 5 | — |
| 9 | 50.00 | 5 | 5 | 5 | 5 | — |
| | 25.00 | 5 | 5 | 5 | 5 | — |
| | 12.50 | 5 | 5 | 5 | 5 | — |
| | 6.25 | 4 | 5 | 4 | 4 | — |
| | 3.125 | 4 | 5 | 4 | 4 | — |
| 10 | 50.00 | 5 | 5 | 5 | 5 | — |
| | 25.00 | 5 | 5 | 5 | 5 | — |
| | 12.50 | 4 | 5 | 4 | 4 | — |
| | 6.25 | 4 | 4 | 4 | 4 | — |
| | 3.125 | 4 | 4 | 4 | 4 | — |
| 11 | 50.00 | 5 | 5 | 5 | 5 | — |
| | 25.00 | 5 | 5 | 5 | 5 | — |
| | 12.50 | 5 | 5 | 4 | 5 | — |

TABLE 2-continued

| Compound No. | Active ingredient (g/a) | Herbicidal efficacy Barnyard grass | Umbrella plant | Bulrush | Waternut grass | Phytotoxicity |
|---|---|---|---|---|---|---|
| | 6.25 | 4 | 4 | 4 | 4 | — |
| | 3.125 | 4 | 4 | 3 | 4 | — |
| 12 | 50.00 | 5 | 5 | 5 | 5 | — |
| | 25.00 | 5 | 5 | 5 | 5 | — |
| | 12.50 | 5 | 5 | 5 | 5 | — |
| | 6.25 | 5 | 5 | 5 | 5 | — |
| | 3.125 | 5 | 5 | 4 | 5 | — |
| 13 | 50.00 | 5 | 5 | 5 | 5 | — |
| | 25.00 | 5 | 5 | 5 | 5 | — |
| | 12.50 | 4 | 5 | 4 | 4 | — |
| | 6.25 | 4 | 4 | 4 | 4 | — |
| | 3.125 | 4 | 4 | 3 | 4 | — |
| 14 | 50.00 | 5 | 5 | 5 | 5 | — |
| | 25.00 | 5 | 5 | 5 | 5 | — |
| | 12.50 | 5 | 5 | 4 | 4 | — |
| | 6.25 | 4 | 5 | 4 | 4 | — |
| | 3.125 | 4 | 4 | 3 | 4 | — |
| 15 | 50.00 | 5 | 5 | 5 | 5 | — |
| | 25.00 | 5 | 5 | 5 | 5 | — |
| | 12.50 | 5 | 5 | 5 | 5 | — |
| | 6.25 | 4 | 5 | 4 | 4 | — |
| | 3.125 | 4 | 4 | 3 | 3 | — |
| 16 | 50.00 | 5 | 5 | 5 | 5 | — |
| | 25.00 | 5 | 5 | 5 | 5 | — |
| | 12.50 | 5 | 5 | 5 | 5 | — |
| | 6.25 | 5 | 5 | 5 | 5 | — |
| | 3.125 | 5 | 5 | 4 | 5 | — |
| 17 | 50.00 | 5 | 5 | 5 | 5 | — |
| | 25.00 | 5 | 5 | 5 | 5 | — |
| | 12.50 | 5 | 5 | 5 | 5 | — |
| | 6.25 | 5 | 5 | 4 | 5 | — |
| | 3.125 | 5 | 5 | 4 | 4 | — |
| A* | 50.00 | 2 | 4 | 3 | 3 | — |
| | 25.00 | 1 | 3 | 2 | 1 | — |
| | 12.50 | 0 | 1 | 1 | 1 | — |
| | 6.25 | 0 | 0 | 0 | 0 | — |
| | 3.125 | 0 | 0 | 0 | 0 | — |
| B* | 50.00 | 4 | 2 | 3 | 4 | — |
| | 25.00 | 3 | 1 | 2 | 3 | — |
| | 12.50 | 2 | 0 | 0 | 1 | — |
| | 6.25 | 1 | 0 | 0 | 0 | — |
| | 3.125 | 0 | 0 | 0 | 0 | — |
| C* | 50.00 | 5 | 5 | 5 | 5 | — |
| | 25.00 | 5 | 5 | 5 | 5 | — |
| | 12.50 | 5 | 5 | 4 | 5 | — |
| | 6.25 | 5 | 5 | 4 | 4 | — |
| | 3.125 | 5 | 5 | 3 | 4 | — |
| D* | 50.00 | 3 | 3 | 2 | 2 | — |
| | 25.00 | 2 | 2 | 1 | 1 | — |
| | 12.50 | 0 | 0 | 0 | 0 | — |
| | 6.25 | 0 | 0 | 0 | 0 | — |
| | 3.125 | 0 | 0 | 0 | 0 | — |
| E* | 50.00 | 5 | 5 | 3 | 3 | — |
| | 25.00 | 5 | 4 | 2 | 2 | — |
| | 12.50 | 3 | 3 | 1 | 2 | — |
| | 6.25 | 2 | 2 | 0 | 0 | — |
| | 3.125 | 2 | 2 | 0 | 0 | — |
| F* | 50.00 | 5 | 4 | 3 | 3 | — |
| | 25.00 | 5 | 4 | 2 | 3 | — |
| | 12.50 | 4 | 2 | 1 | 1 | — |
| | 6.25 | 3 | 1 | 0 | 0 | — |
| | 3.125 | 3 | 1 | 0 | 0 | — |
| Non-treated | — | 0 | 0 | 0 | 0 | — |

*The compounds A to E are for comparison, and have the following meanings

A: 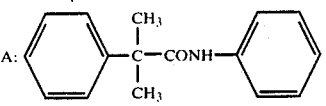

Chemical Abstracts, Vol. 48 (1954) 8193b

B: 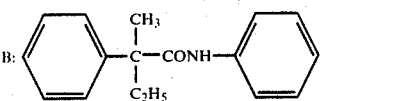

C: 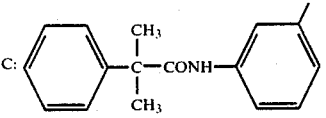

U.S. Pat. No. 4,453,975

D: 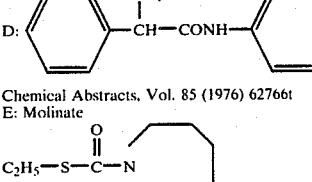

Chemical Abstracts, Vol. 85 (1976) 62766t
E: Molinate

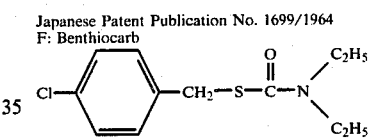

Japanese Patent Publication No. 1699/1964
F: Benthiocarb

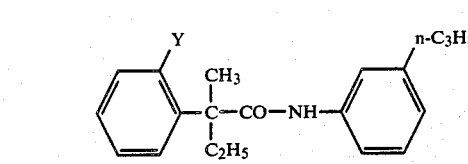

Japanese Patent Publication No. 29024/1968

What we claim is:
1. A compound of the formula

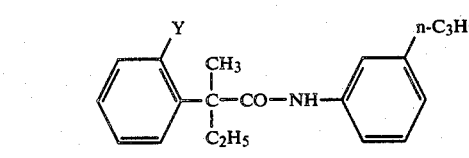

wherein Y represents fluoro, methyl or methoxy.
2. The compound according to claim 1 wherein Y represents fluoro.
3. The compound according to claim 1 wherein Y represents methyl.
4. The compound according to claim 1 wherein Y represents methoxy.
5. A herbicidal composition comprising a herbicidally effective amount of a compound of the formula:

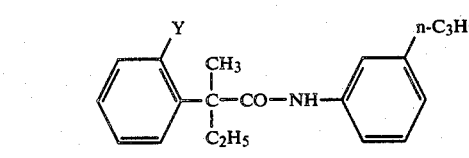

wherein Y represents fluoro, methyl or methoxy and an inert liquid or solid carrier or diluent.
6. The herbicidal composition according to claim 5 wherein Y is fluoro.
7. The herbicidal composition according to claim 5 whereby Y is methyl.
8. The herbicidal composition according to claim 5 wherein Y is methoxy.

* * * * *